(12) United States Patent
Herrmann et al.

(10) Patent No.: US 10,868,074 B2
(45) Date of Patent: Dec. 15, 2020

(54) DETECTOR MODULE, DETECTOR, IMAGING APPARATUS AND METHOD OF MANUFACTURING A DETECTOR MODULE

(71) Applicant: KONINKLIJKE PHILIPS N.V., Eindhoven (NL)

(72) Inventors: Christoph Herrmann, Aachen (DE); Roger Steadman Booker, Aachen (DE); Amir Livne, Zichron Ya'Aqov (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/316,051

(22) PCT Filed: Jul. 14, 2017

(86) PCT No.: PCT/EP2017/067852
§ 371 (c)(1),
(2) Date: Jan. 8, 2019

(87) PCT Pub. No.: WO2018/011399
PCT Pub. Date: Jan. 18, 2018

(65) Prior Publication Data
US 2019/0280036 A1    Sep. 12, 2019

(30) Foreign Application Priority Data

Jul. 14, 2016  (EP) .................................... 16179411

(51) Int. Cl.
*G01T 1/24*       (2006.01)
*H01L 27/146*     (2006.01)
*A61B 6/03*       (2006.01)

(52) U.S. Cl.
CPC ........ *H01L 27/14636* (2013.01); *A61B 6/035* (2013.01); *G01T 1/24* (2013.01);
(Continued)

(58) Field of Classification Search
CPC ......... H01L 27/14636; H01L 27/14618; H01L 27/1469; H01L 27/14634; H01L 27/14659; H01L 27/14661; G01T 1/24
See application file for complete search history.

(56) References Cited

U.S. PATENT DOCUMENTS

2005/0286682 A1* 12/2005 Tkaczyk ............... G01T 1/2018
378/98.8
2007/0034807 A1   2/2007 Danzer
(Continued)

FOREIGN PATENT DOCUMENTS

JP    2002158341    5/2002
WO   2013050229    4/2013
(Continued)

OTHER PUBLICATIONS

Richard Bijlard, "No-Compromise multi-material solutions with ATB ambient temperature bonding", CMN vol. 8 No. 7, Nov. 29, 2015.

*Primary Examiner* — Kiho Kim
(74) *Attorney, Agent, or Firm* — Larry Liberchuk (57) ABSTRACT

The present invention relates to a detector module comprising a direct conversion crystal (10) for converting incident photons into electrical signals, said direct conversion crystal having a cathode metallization (100) deposited on a first surface and an anode metallization (101) deposited on a second surface, an integrated circuit (12) in electrical communication with said direct conversion crystal, said integrated circuit having a smaller width than said direct conversion crystal thus forming a recess (120) in width direction at a side surface of the integrated circuit, an interposer (11, 11*a*) arranged between said direct conversion crystal and said integrated circuit for providing electrical communication there between, wherein said interposer is made as separate element that is glued, soldered or bonded with the
(Continued)

anode metallization (101) of said direct conversion crystal facing said integrated circuit, and a multi-lead flex cable (13, 13*a*, 13*b*, 13*c*, 13*d*) providing a plurality of output paths, said multi-lead flex cable having a first portion (131, 131*a*, 131*b*, 131*c*, 13 1*d*) connected with one surface to said direct conversion crystal and with the opposite surface to said integrated circuit (12) and a second portion (132), which is bent with respect to the first portion and is arranged in said recess.

13 Claims, 4 Drawing Sheets

(52) U.S. Cl.
CPC .... *H01L 27/1469* (2013.01); *H01L 27/14618* (2013.01); *H01L 27/14634* (2013.01); *H01L 27/14659* (2013.01); *H01L 27/14661* (2013.01)

(56) References Cited

U.S. PATENT DOCUMENTS

| | | |
|---|---|---|
| 2009/0080601 A1 | 3/2009 | Tkaczyk |
| 2010/0327173 A1* | 12/2010 | Woychik ................ H01L 25/16 250/370.09 |
| 2013/0049151 A1* | 2/2013 | Lobastov .......... H01L 27/14659 257/432 |
| 2014/0334601 A1* | 11/2014 | Shizukuishi ...... H01L 27/14661 378/62 |

FOREIGN PATENT DOCUMENTS

| | | |
|---|---|---|
| WO | 2013/176657 | 11/2013 |
| WO | 2016/066850 | 5/2016 |

\* cited by examiner

DETECTOR MODULE, DETECTOR, IMAGING APPARATUS AND METHOD OF MANUFACTURING A DETECTOR MODULE

CROSS REFERENCE TO RELATED APPLICATIONS

This application is the U.S. National Phase application under 35 U.S.C. § 371 of International Application No. PCT/EP2017/067852 filed Jul. 14, 2017, published as WO 2018/011399 on Jan. 18, 2018, which claims the benefit of European Patent Application Number 16179411.0 filed Jul. 14, 2016. These applications are hereby incorporated by reference herein.

FIELD OF THE INVENTION

The present invention relates to a detector module, a detector, an imaging apparatus and a method of manufacturing a detector module.

BACKGROUND OF THE INVENTION

Detector modules with 4-side-buttability are a prerequisite to build large area detectors as used in X-ray and CT imaging apparatus, e.g. for medical or industrial imaging. For energy-integrating detectors this problem is solved by using a (ceramic) interposer that provides redistribution of the photodiode array anode contacts to the integrated circuit (generally an ASIC), which is smaller than the (back-illuminated) photodiode array. In a more advanced approach, the redistribution function is implemented on top of the photodiode array anode so that the (expensive) ceramic interposer can be avoided. The more advanced approach results in short track lengths between an anode contact and the corresponding input pad on the ASIC. Although the shorter track length reduces the capacitive load seen by the input pad of the ASIC and therefore helps to reduce noise, available analogue readout channels can easily deal with the SNR caused by the long track lengths. Shorter track lengths may allow to reduce the ASIC's power consumption, since the SNR is higher due to the reduced capacitive load.

For a photon counting spectral detector, as e.g. used in a CT system, long track lengths between the direct converter crystal (e.g. CZT) sensor pixel and the input pad of the read-out ASIC are not tolerable, since the resulting noise would limit the energy separation capabilities in an unacceptable way; very fast analogue amplifiers and significantly more pixels per area limit power available per pixel so that only a smaller capacitive load can be tolerated than in energy-integrating readout systems. More importantly however, long tracks will also cause inter-pixel cross-talk depending on the pixel activity.

A straight-forward approach to provide interconnect with minimum track-length is to design the ASIC with TSVs (through-silicon vias). Although for certain high-volume products (mobile phone cameras, stacked memory devices, . . . ) TSVs are cheaply available, for the comparably low volumes of sophisticated medical imaging devices TSVs are not readily available at an acceptable price. In addition, with TSVs the ASIC has to be as large as the sensor, even though the electronics for the pixels and the electronics common to all pixels may not need all the space available in the chosen CMOS technology so that expensive die area may somewhat be wasted just to support the backside contacting provided by TSVs. Finally, in order to get to ASICs with sufficient thickness with TSVs to make them mechanically robust, which is helpful during assembly, TSV processing has to be done after the CMOS processing, which often requires a second supplier.

US 2010/327173 A1 discloses a detector module comprising a direct conversion crystal for converting incident photons into electrical signals, the direct conversion crystal having an anode layer deposited on a first surface and a cathode layer deposited on a second surface, a redistribution layer deposited on the anode layer, the redistribution layer configured to adapt a pad array layout of the direct conversion crystal to a predetermined lead pattern, an integrated circuit in electrical communication with the direct conversion crystal, and a plurality of input/output electrical paths connected to the redistribution layer to provide connectivity between the imaging module and another level of interconnect. A flex pig-tail may be soldered to one or more corresponding redistribution perimeter pads on the redistribution layer to provide a plurality of input/output electrical paths for the integrated circuit.

US 2009/080601 A1 discloses a CT detector including a direct conversion material configured to generate electrical charge upon reception of x-rays, a plurality of metallized anodes configured to collect electrical charges generated in the direct conversion material, at least one readout device, and a redistribution layer having a plurality of electrical pathways configured to route the electrical charges from the plurality of metallized anodes to the at least one readout device.

WO 2016/066850 A1 discloses a sensor device for detecting radiation signals. To enable high signal integrity and cost efficiency while maintaining the capability of being four-sidedly buttable, the sensor device comprises a sensor array comprising a plurality of detectors, a sensor element for converting said received radiation signals into a plurality of corresponding electric signals, an interposer element extending laterally between a first side and a second side, and an integrated circuit element.

SUMMARY OF THE INVENTION

It is an object of the present invention to provide a detector module that enables 4-side-buttability without the use of TSVs but can be easily and inexpensively manufactured. It is a further object of the present invention to provide a detector, an imaging apparatus and a method of manufacturing a detector module.

In a first aspect of the present invention a detector module is presented comprising a direct conversion crystal for converting incident photons into electrical signals, said direct conversion crystal having a cathode metallization deposited on a first surface and an anode metallization deposited on a second surface, an integrated circuit in electrical communication with said direct conversion crystal, said integrated circuit having a smaller width than said direct conversion crystal thus forming a recess in width direction at a side surface of the integrated circuit, an interposer arranged between said direct conversion crystal and said integrated circuit for providing electrical communication there between, wherein said interposer is made as separate element that is glued, soldered or bonded with the anode metallization of said direct conversion crystal facing said integrated circuit, and a multi-lead flex cable providing a plurality of output paths, said multi-lead flex cable having a first portion connected with one surface to said direct conversion crystal and with the opposite surface to said integrated circuit and a second portion, which is bent with respect to the first portion and is arranged in said recess.

In a further aspect of the present invention a detector is presented comprising a plurality of detector modules as disclosed herein, arranged adjacent to each other to form a planar array of detector modules.

In a further aspect of the present invention an imaging apparatus is presented comprising a detector as disclosed herein.

In a further aspect of the present invention a method of manufacturing a detector module is presented comprising
making an interposer as a separate element,
contacting by gluing, soldering or bonding said interposer to an anode metallization of a direct conversion crystal that is configured for converting incident photons into electrical signals, said direct conversion crystal having a cathode metallization deposited on a first surface and an anode metallization deposited on a second surface,
arranging an integrated circuit on a surface side of the interposer facing away from said direct conversion crystal, the interposer providing electrical communication between said integrated circuit and said direct conversion crystal, said integrated circuit having a smaller width than said direct conversion crystal thus forming a recess in width direction at a side surface of the integrated circuit,
arranging a multi-lead flex cable in said recess, said multi-lead flex cable providing a plurality of output paths, wherein a first portion of said multi-lead flex cable is connected with one surface to said direct conversion crystal and with the opposite surface to said integrated circuit and a second portion, which is bent with respect to the first portion, is arranged in said recess.

Preferred embodiments of the invention are defined in the dependent claims. It shall be understood that the claimed detector, imaging apparatus and method have similar and/or identical preferred embodiments as the claimed detector module, in particular as defined in the dependent claims and as disclosed herein.

One of the elements of the present invention is a thin multi-lead flex cable, which allows for a small bending radius. Due to the small bending radius, only little space is needed for accommodating the flex cable so that the space between adjacent detector modules can be minimized or kept very small (e.g. 200 μm) since the flex cable can, at least partly (i.e. a second portion of it) be arranged in a recess formed in the integrated circuit.

Another element of the present invention is the construction of the interposer, which is particularly a tailored interposer that minimizes the track lengths, as separate element, which is mounted to the anode metallization of the direct conversion crystal in a separate manufacturing step, i.e. the interposer is not deposited to the anode metallization of the direct conversion crystal. Depositing a redistribution layer on a direct conversion crystal is complicated, since the crystal material often limits the maximum allowed processing temperature; if this limit is exceeded, the imaging performance of the crystal deteriorates. Hence, according to the present invention, a different handling of the various elements and a different manufacturing technology is used for manufacturing the detector module compared to the manufacturing of the detector module disclosed in US 2010/327173 A1.

According to the invention said interposer is glued, soldered or bonded to the anode metallization of said direct conversion crystal facing said integrated circuit. This may generally include any forms of gluing, soldering and bonding, including e.g. thermo-compression bonding, room-temperature bonding, stud-bump bonding combined with gluing, etc. These ways of forming a contact and mounting an element to another element are inexpensive and allow easy handling of the elements.

In another preferred embodiment said integrated circuit is glued, soldered or bonded to a surface of said interposer facing said integrated circuit. In this case, the first portion of the flex cable is generally short and only arranged at an edge portion between the interposer and the integrated circuit.

In another embodiment said interposer comprises a cavity and the first portion of said multi-lead flex cable is at least partly arranged in said cavity. This provides for a space-saving arrangement.

The interposer is preferably configured as rigid element, which provides for stability of the detector module.

In an embodiment the first portion of said multi-lead flex cable is interposed between said interposer and said integrated circuit for providing electrical communication there between, preferably across the complete width of said integrated circuit. This further improves stability. The multi-lead flex cable may thus also be used for redistributing the signals between the interposer and the integrated circuit.

In another embodiment the first portion and said interposer are integrated forming a flex interposer. The redistribution can thus be provided inside the flex interposer.

Preferably, the detector module further comprises a heat sink arranged on a surface of said integrated circuit facing away from said interposer. This provides for cooling of the detector module, in particular the integrated circuit.

The first portion of said multi-lead flex cable may be glued, soldered or bonded to a surface of said interposer facing said integrated circuit.

In still another embodiment the first portion of said multi-lead flex cable or said interposer comprises redistribution connections for connecting crystal pixel contacts of said direct conversion crystal with integrated circuit pixel contacts of said integrated circuit. This provides a simple but efficient way of providing the connections between said different pixels.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
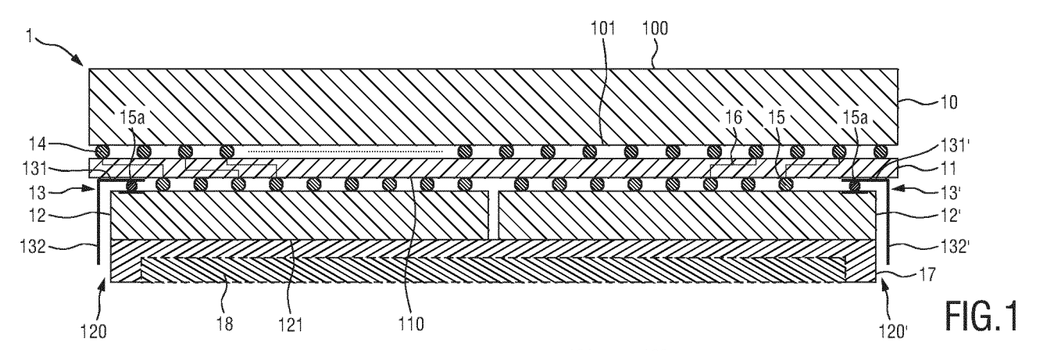
FIG. 1 shows a cross-sectional view of a first embodiment of a detector module.

FIG. 1 shows a cross-sectional view of a first embodiment of a detector module 1. It comprises a direct conversion crystal 10 (also called DiCo in the following), e.g. made of CZT and/or CdTe or other material, for converting incident photons into electrical signals. The direct conversion crystal has a cathode metallization 100 (also called cathode layer) deposited on a first surface and an anode metallization 101 (also called anode layer) deposited on a second surface.

The detector module 1 further comprises an integrated circuit 12 (e.g. an ASIC) in electrical communication with said direct conversion crystal 10. In this embodiment two integrated circuits 12, 12' are provided, each having a recess 120, 120', but this is generally not required. The integrated circuit has a smaller width than said direct conversion crystal and thus forms a recess 120 in width direction at one side surface.

An interposer 11 is arranged between said direct conversion crystal 10 and said integrated circuit(s) 12, 12' for providing electrical communication there between. The interposer 11 is a rigid element and is made as separate element that is contacted with the anode metallization 101 of the direct conversion crystal 10 facing said integrated circuit(s) 12, 12'. In this embodiment, the interposer 11 is soldered to the anode metallization 101 of said direct conversion crystal 10 by solder balls 14. The interposer 11 is further soldered to the surface of the ASICs 12, 12' facing the direct conversion crystal 10 by solder balls 15. Other ways of forming the connection than soldering are possible, as long as the interposer 11 can be formed and handled as separate element. For instance, any forms of gluing, soldering and bonding, including e.g. thermo-compression bonding, room-temperature bonding, stud-bump bonding, etc., may be used.

Preferably, the rigid interposer 11 has a redistribution function and may also be called RDL interposer. For this purpose it comprises redistribution connections 16. The rigid interposer 11 thus connects the pixel contacts of the ASICs 12, 12' to the pixels of the direct conversion crystal 10.

A multi-lead flex cable 13, 13' is provided (in this embodiment two flex cables 13, 13' are provided, which is not generally required) that provides a plurality of output paths. The multi-lead flex cables 13, 13' each have a first portion 131, 131' connected to said direct conversion crystal 10 and a second portion 132, 132', which is bent with respect to the first portion 131, 131'. Said first portion 131, 131' is arranged in a direction along the width of the integrated circuit and perpendicular to the length of the integrated circuit. Said second portion 132, 132' is arranged in the respective recess 120, 120'. The flex cables (e.g. with Cu tracks) 13, 13' can be made e.g. of polyimide and can thus have a very small bending radius. The flex cables 13, 13' contact the ASIC I/O/P (Input/Output/Power) pads, which connect the ASICs 12, 12' to the outside world.

In order to do the contacting by means of solder balls, both a hierarchy in ball size and in melting temperature may be applied. The hierarchy in temperature can be achieved with different soldering alloys: The flex cables 13, 13' are first soldered with an alloy 15a melting at T1, then the interposer 11 is contacted to the pixels of the ASICs 12, 12' with solder balls 15 melting at T2<T1, and in the last step the DiCo crystal 10, which anyway has to be processed at low temperatures, is contacted to the top side pads of the interposer 11 with solder balls 14 melting at T3<T2.

Optionally, as shown in FIG. 1, a common heat sink 17, e.g. an Aluminum block, is arranged on a surface 121 of the ASICs 12, 12' facing away from said interposer 11. From the surface side facing away from the ASICs 12, 12' airflow 18 can be provided for cooling purposes.

Figure 2:
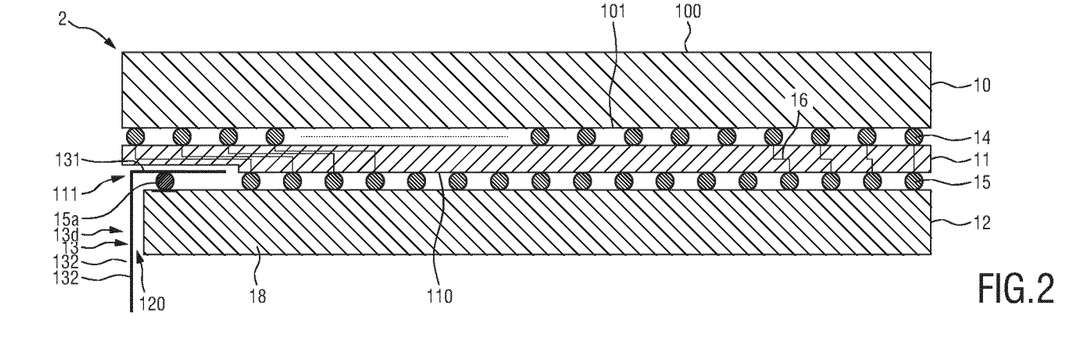
FIG. 2 shows a cross-sectional view of a second embodiment of a detector module.

FIG. 2 shows a cross-sectional view of a second embodiment of a detector module 2. Different from the first embodiment of the detector module 1, the detector module 2 comprises a single ASIC 12 and a single flex cable 13. A cavity 111 is formed in the surface 110 of the interposer 11. In the cavity 111 the first portion 131 of the flex cable 13 is arranged. The cavity 1 may increase cost of the interposer 11, but in this embodiment of the detector module 2 only a hierarchy in melting temperature is needed, since a cavity 111 (or milled down region) in the interposer 11 provides the required space to use the same ball size for the solder balls 15 and 15a.

With the short flex cable 11, 11' of the detector modules 1 and 2 the mechanical stability is limited since the few solder balls 15a have to accept the forces applied in the bending process of bending the flex cable 11, 11'. The rigid RDL interposer 11 can e.g. be made of ceramic or glass.

Figure 3:
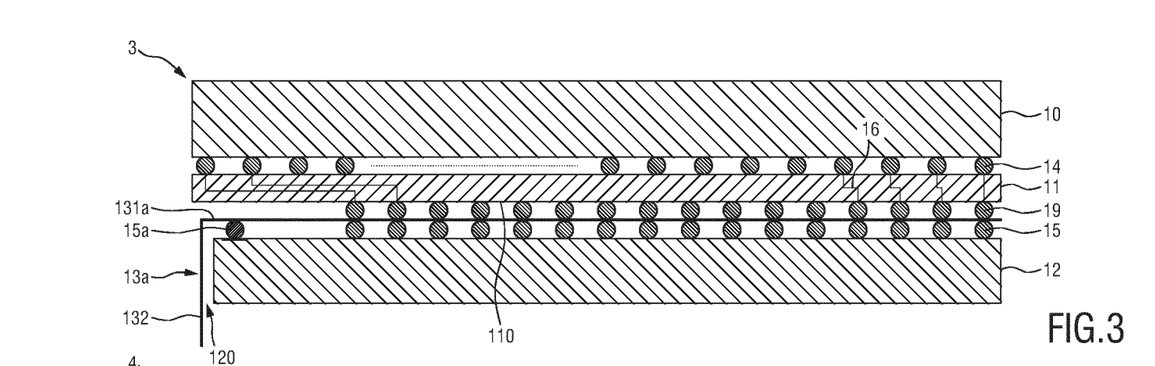
FIG. 3 shows a cross-sectional view of a third embodiment of a detector module.

FIG. 3 shows a cross-sectional view of a third embodiment of a detector module 3, which comprises a 1-to-1 interposer (i.e. without RDL function) made of flex material. This 1-to-1 interposer 131a is hereby formed by the first portion of the flex cable 13a. On top of the 1-to-1 interposer 131a a rigid RDL interposer 11 is mounted by soldering using solder balls 19.

The flex cable 13a still fulfills the purpose of bringing the I/O/P contacts to the outside world of the detector module 3. On top of the RDL interposer 11 the DiCo material 10 is soldered by solder balls 14. In this case due to the very long flex cable 13a, the mechanical stability of the flexible part is maximized. A drawback may be the two sets of solder balls 15, 19 below and above the 1-to-1 interposer 131a. Also in this embodiment a melting temperature hierarchy with three different melting temperatures may be required.

Figure 4:
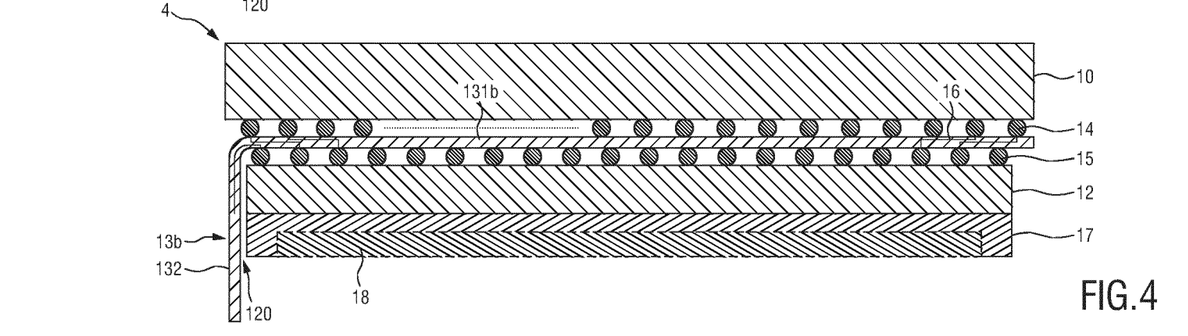
FIG. 4 shows a cross-sectional view of a fourth embodiment of a detector module.

FIG. 4 shows a cross-sectional view of a fourth embodiment of a detector module 4. The flexible interposer 131b (i.e. the first portion of the flex cable 13b) also implements the RDL function in this embodiment, i.e. it combines the function of the first portion of the flex cable (the 1-to-1 interposer) and the rigid interposer. Such a detector module 4 may even show better cross-talk reduction than the detector module using a rigid RDL interposer if it is made of ceramic.

The connection by the row of solder balls 14 between the DiCo crystal 10 and the flex interposer 131b has to withstand the forces exerted during bending, which is critical in two respects: the solder connection can break and/or the rather brittle DiCo crystal 10 can be damaged during bending and/or crystal material can be torn out of DiCo crystal block. Furthermore, due to the proximity to the DiCo crystal edge of the connecting solder ball, the required inter-module space (i.e. the space between adjacent detector modules) may be somewhat larger than in the first embodiments, in which the rigid interposer 11 extends over the ASIC 12 and "protects" this first row of solder balls 14 between the interposer 11 and the DiCo crystal 10. This is particularly the case if the first row of DiCo crystal anodes is very close to the edge of the DiCo crystal 10. Since the DiCo crystal anodes are generally much larger than the area for the interconnection, the solder mask in the first row may be shifted toward the inner side of the DiCo crystal for the purpose of gaining some space for the bending. That is, the pitch of the anodes is kept, but the solder balls 14 on the first row are purposely shifted resulting in a slightly smaller pitch to the subsequent row.

Figure 5:
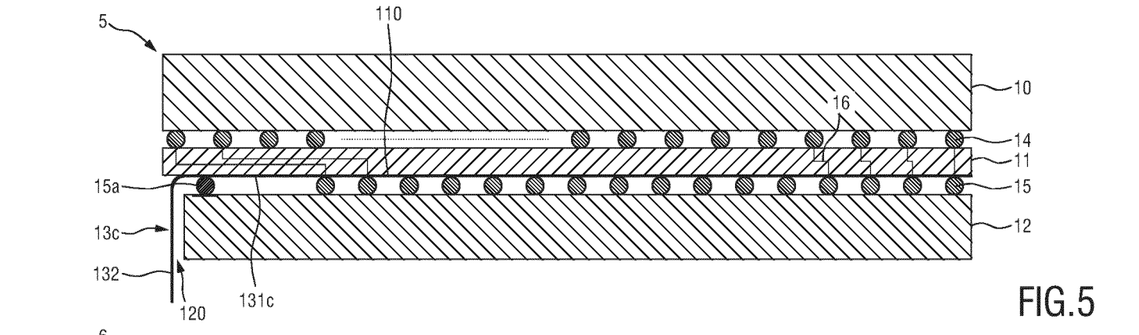
FIG. 5 shows a cross-sectional view of a fifth embodiment of a detector module.

FIG. 5 shows a cross-sectional view of a fifth embodiment of a detector module 5. In this embodiment the latter problem is even more elegantly solved by bonding a 1-to-1 flex cable 13c, in particular its first portion 131c, to a rigid RDL interposer 11. A number of methods exist in order to obtain such a bond, which include:

Glue both substrates with ACF (anisotropic conductive glue), as long as the resulting series resistance is kept low (e.g. <10 Ohm);

Thermo-compression bonding;

Room-temperature bonding (as offered by commercial suppliers); in this bonding process, a laser locally heats up the surfaces of the two parts that touch each other resulting in a plasma layer which then forms a bond. This process does not only bond the substrates but also creates electrical connections (cf. "No-Compromise multi-material solutions with ATB ambient temperature bonding". Richard Bijlard, CMN Vol. 8 No. 7).

The rigid RDL interposer 11 well protects the first row of solder balls 14. A drawback may be the larger crosstalk capacitance of the rigid RDL interposer 11, if it is manufactured in ceramic with the limitation of the allowed density of tracks mentioned above; the combination of an RDL interposer made of glass bonded to a flex 1-to-1 interposer 13c would provide lower cross-coupling capacitances, thus being the a good solution since the DiCo crystal 10 is protected well against the force during bending, and pulling solder balls off the DiCo crystal 10 is prevented by the interposer 11.

Figure 6:
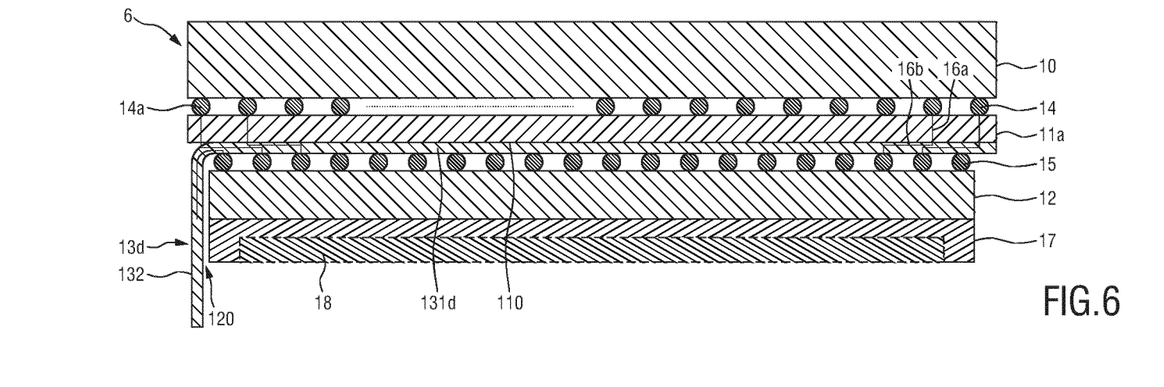
FIG. 6 shows a cross-sectional view of a sixth embodiment of a detector module.

FIG. 6 shows a cross-sectional view of a sixth embodiment of a detector module 6, which makes use of the opposite combination, i.e. a flex RDL interposer 131d low-temperature-bonded to a rigid 1-to-1 interposer 11a. This offers an advantage in terms of reduced cross-talk capacitance of a flex interposer and eliminates the risk of damaging the brittle DiCo crystal 10 due to bending. It may still have the problem that during bending the force exerted to the first row 14a of solder balls 14 damages the bond connection between 1-to-1 interposer 11a (made of ceramic or glass) and flex cable 13d. By introducing small RDL functionality in the 1-to-1 interposer 11a only at the first row 14a, this problem can be mitigated significantly. In this option, a ceramic 1-to-1 interposer 11a can be used in combination with a flex cable 13d; glass may not be reliable enough on a rotating gantry due to its mechanical properties.

Figure 7:
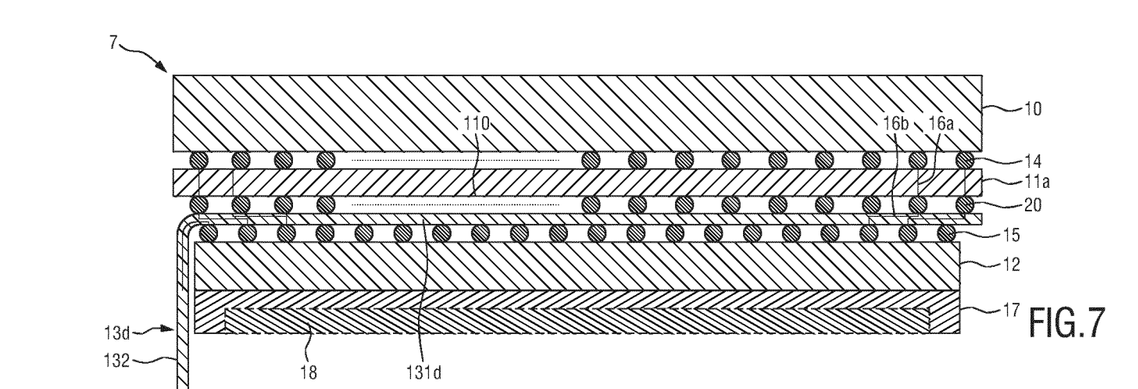
FIG. 7 shows a cross-sectional view of a seventh embodiment of a detector module.

FIG. 7 shows a cross-sectional view of a seventh embodiment of a detector module 7. In this embodiment the flex interposer 131d is contacted to the rigid interposer 11a by a row of solder balls 20.

Figure 8:
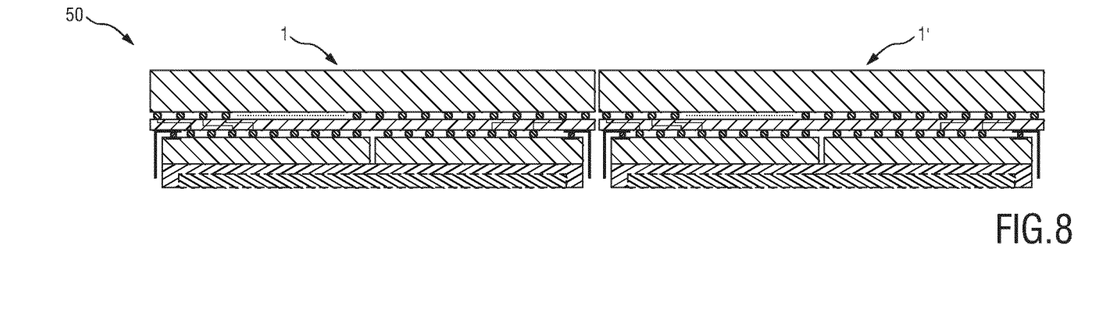
FIG. 8 shows a cross-sectional view of an embodiment of a detector including two detector modules according to the first embodiment.

FIG. 8 shows a cross-sectional view of an embodiment of a detector 50 including two detector modules 1, 1' according to the first embodiment) (alternatively according to any other embodiment). As shown in FIG. 8, the detector modules 1, 1' can be arranged adjacent to each other very close to each other with almost no empty space in between.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A detector module comprising:
a direct conversion crystal for converting incident photons into electrical signals, said direct conversion crystal having a cathode metallization deposited on a first surface and an anode metallization deposited on a second surface,
an integrated circuit in electrical communication with said direct conversion crystal, said integrated circuit having a smaller width than said direct conversion crystal thus forming a recess in width direction at a side surface of the integrated circuit,
an interposer arranged between said direct conversion crystal and said integrated circuit for providing electrical communication there between, wherein said interposer is made as separate element that is glued, soldered or bonded with the anode metallization of said direct conversion crystal facing said integrated circuit, and
a multi-lead flex cable providing a plurality of output paths, said multi-lead flex cable having a first portion connected with one surface to said interposer and with the opposite surface to said integrated circuit and having a second portion, which is bent with respect to the first portion and is arranged in said recess.

2. The detector module as claimed in claim 1, wherein said integrated circuit is glued, soldered or bonded to a surface of said interposer facing said integrated circuit.

3. The detector module as claimed in claim 1, wherein said interposer comprises a cavity and the first portion of said multi-lead flex cable is at least partly arranged in said cavity.

4. The detector module as claimed in claim 1, wherein said interposer is configured as rigid element.

5. The detector module as claimed in claim 1, wherein the first portion of said multi-lead flex cable is interposed between said interposer and said integrated circuit for providing electrical communication there between.

6. The detector module as claimed in claim 5, wherein the first portion of said multi-lead flex cable is interposed between said interposer and said integrated circuit across a complete width of said integrated circuit.

7. The detector module as claimed in claim 5, wherein the first portion of said multi-lead flex cable is glued, soldered or bonded to a surface of said interposer facing said integrated circuit.

8. The detector module as claimed in claim 1, wherein the first portion and said interposer are integrated forming a flex interposer.

9. The detector module as claimed in claim 1, further comprising a heat sink arranged on a surface of said integrated circuit facing away from said interposer.

10. The detector module as claimed in claim 1, wherein the first portion of said multi-lead flex cable or said interposer comprises redistribution connections for connecting crystal pixel contacts of said direct conversion crystal with integrated circuit pixel contacts of said integrated circuit.

11. A detector comprising:
a plurality of detector modules, each detector module of the plurality of detector modules comprises:
a direct conversion crystal for converting incident photons into electrical signals, said direct conversion crystal having a cathode metallization deposited on a first surface and an anode metallization deposited on a second surface,
an integrated circuit in electrical communication with said direct conversion crystal, said integrated circuit having a smaller width than said direct conversion crystal thus forming a recess in width direction at a side surface of the integrated circuit,
an interposer arranged between said direct conversion crystal and said integrated circuit for providing electrical communication there between, wherein said interposer is made as separate element that is glued, soldered or bonded with the anode metallization of said direct conversion crystal facing said integrated circuit, and
a multi-lead flex cable providing a plurality of output paths, said multi-lead flex cable having a first portion connected with one surface to said interposer and with the opposite surface to said integrated circuit and having a second portion, which is bent with respect to the first portion and is arranged in said recess, and
wherein detector modules of the plurality of detector modules are arranged adjacent to each other to form a planar array of detector modules.

12. An imaging apparatus comprising a detector as claimed in claim 11.

13. A method of manufacturing a detector module, the detector module includes:
a direct conversion crystal for converting incident photons into electrical signals, said direct conversion crystal having a cathode metallization deposited on a first surface and an anode metallization deposited on a second surface,
an integrated circuit in electrical communication with said direct conversion crystal, said integrated circuit having a smaller width than said direct conversion crystal thus forming a recess in width direction at a side surface of the integrated circuit,
an interposer arranged between said direct conversion crystal and said integrated circuit for providing electrical communication there between, wherein said interposer is made as separate element that is glued, soldered or bonded with the anode metallization of said direct conversion crystal facing said integrated circuit, and
a multi-lead flex cable providing a plurality of output paths, said multi-lead flex cable having a first portion connected with one surface to said interposer and with the opposite surface to said integrated circuit and having a second portion, which is bent with respect to the first portion and is arranged in said recess, said method comprising:
making an interposer as a separate element,
contacting by gluing, soldering or bonding said interposer to an anode metallization of a direct conversion crystal that is configured for converting incident photons into electrical signals, said direct conversion crystal having a cathode metallization deposited on a first surface and an anode metallization deposited on a second surface,
arranging an integrated circuit on a surface side of the interposer facing away from said direct conversion crystal, the interposer providing electrical communication between said integrated circuit and said direct conversion crystal, said integrated circuit having a smaller width than said direct conversion crystal thus forming a recess in width direction at a side surface of the integrated circuit,
arranging a multi-lead flex cable in said recess, said multi-lead flex cable providing a plurality of output paths, wherein a first portion of said multi-lead flex cable is connected with one surface to said interposer and with the opposite surface to said integrated circuit and a second portion, which is bent with respect to the first portion, is arranged in said recess.

* * * * *